United States Patent
Yang et al.

(10) Patent No.: US 12,024,743 B2
(45) Date of Patent: Jul. 2, 2024

(54) METHODS, PROCEDURES AND KITS FOR PROVIDING MAXIMUM DEPTH ENRICHMENT SEQUENCING FOR IDENTIFICATION FOR ENRICHMENT OF RARE GENOMIC VARIANTS

(71) Applicant: NEW YORK UNIVERSITY, New York, NY (US)

(72) Inventors: Kevin Brendan Yang, New York, NY (US); Evgeny Nudler, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 250 days.

(21) Appl. No.: 17/236,683

(22) Filed: Apr. 21, 2021

(65) Prior Publication Data

US 2021/0332429 A1    Oct. 28, 2021

Related U.S. Application Data

(60) Provisional application No. 63/013,927, filed on Apr. 22, 2020.

(51) Int. Cl.
| | |
|---|---|
| *C12Q 1/6869* | (2018.01) |
| *C12N 9/22* | (2006.01) |
| *C12Q 1/6844* | (2018.01) |
| *C12Q 1/6853* | (2018.01) |
| *C12Q 1/686* | (2018.01) |

(52) U.S. Cl.
CPC ............ *C12Q 1/6869* (2013.01); *C12N 9/22* (2013.01); *C12Q 1/6846* (2013.01); *C12Q 1/6853* (2013.01); *C12Q 1/686* (2013.01); *C12N 2310/20* (2017.05)

(58) Field of Classification Search
CPC .. C12Q 1/6869; C12Q 1/6846; C12Q 1/6853; C12Q 1/686; C12Q 1/6806; C12Q 1/6848; C12Q 2525/161; C12Q 2525/191; C12Q 2531/101; C12Q 2535/122; C12Q 2563/179; C12Q 2565/102; C12Q 2537/159; C12N 9/22; C12N 2310/20
See application file for complete search history.

(56) References Cited

U.S. PATENT DOCUMENTS

| | | | |
|---|---|---|---|
| 2017/0016062 A1 | 1/2017 | Jee et al. | |
| 2020/0020417 A1* | 1/2020 | Schnall-Levin | ....... G16B 30/10 |

FOREIGN PATENT DOCUMENTS

| | | |
|---|---|---|
| EP | 2107124 A1 | 7/2009 |

OTHER PUBLICATIONS

The TRACERx consortium et al. Phylogenetic ctDNA analysis depicts early-stage lung cancer evolution. Nature 545, 446-451 (2017).
Jee, J. et al. Rates and mechanisms of bacterial mutagenesis from maximum-depth sequencing. Nature 534, 693-6 (2016).
Song, C. Elimination of unaltered DNA in mixed clinical samples via nuclease-assisted minor-allele enrichment. Nucleic Acids Res. 44(19): e146 (2016).

* cited by examiner

*Primary Examiner* — Narayan K Bhat
(74) *Attorney, Agent, or Firm* — HUNTON ANDREWS KURTH LLP

(57) ABSTRACT

Exemplary embodiments of methods, kits, systems and computer-accessible medium can be provided for facilitating maximum depth enrichment sequencing for identifying rare genomic variants.

7 Claims, 3 Drawing Sheets

METHODS, PROCEDURES AND KITS FOR PROVIDING MAXIMUM DEPTH ENRICHMENT SEQUENCING FOR IDENTIFICATION FOR ENRICHMENT OF RARE GENOMIC VARIANTS

CROSS REFERENCE TO RELATED APPLICATIONS

This application relates to and claims priority from U.S. Provisional Patent Application Ser. No. 63/013,927, filed Apr. 22, 2020, the disclosure of which is incorporated herein by reference in its entirety.

FIELD OF THE DISCLOSURE

The present disclosure is directed to exemplary methods, kits, systems and computer-accessible medium for providing maximum depth enrichment sequencing in combination with DNA barcoding for an enrichment of rare genomic variants.

BACKGROUND INFORMATION

There are several existing methods that correct for error rates intrinsic in library preparation and sequencing, including duplex sequencing and Maximum Depth Sequencing (MDS). These methods use degenerate molecular tags, otherwise known as "barcodes", to label redundant copies of an original genomic molecule. Following sequencing, these barcodes can be used to form a consensus sequence that is robust to polymerase and sequencing errors, decreasing error rates from 1E-2 to 1E-6 and below. These advances have given scientists the ability to detect extremely rare genomic variants in a population, increasing sensitivity in cancer prognosis and bacterial metagenomics. However, these techniques all have a major shortcoming in searching for rare mutants. Because these mutants are rare, they are by definition a small proportion of a larger wild-type fraction. To detect a mutant that exists at a frequency of 1E-6, one million normal sequences need to be sequenced to identify a single mutant sequence. Thus, a large amount of sequencing space is wasted in addition to the excess coverage already necessary for implementing any type of barcoding.

Despite steadily decreasing sequencing costs over the past two decades, detection of rare mutants is still incredibly expensive. A recent study detecting rare variants in the blood of lung cancer patients estimated a cost of $1,750 per region of interest, per patient as of 2017 (See TRACERx Consortium et al. Phylogenetic ctDNA analysis depicts early-stage lung cancer evolution. *Nature* 545, 446-451 (2017). This is simply unaffordable in managing patients known to have cancer, especially since multiple samples are collected throughout the disease course and several tumor regions must be examined. It is even less unrealistic in early screening applications, where a large panel of hundreds of tumor hot spots need to be surveyed.

Moreover, barcoding techniques can only successfully form consensus sequences for a limited number of original genomic molecules. It is only reasonable to screen less than half a million cells—costs linearly increase with the number of desired genomes—and a normal laboratory blood draw contains 10 million nucleated cells. Therefore, in most reasonable use cases, current technologies are only sensitive to 5E-5 and can only utilize 5% of the information in a single blood draw.

Clearly there is need for providing methods, systems and computer-accessible medium that address at least some of the deficiencies described herein while preserving the error correction afforded by barcoding.

EXEMPLARY SUMMARY OF THE DISCLOSURE

Such need is addressed with the exemplary methods, kits, systems and computer-accessible medium described herein.

For example, in one exemplary embodiment, a method can be provided for sequencing a nucleic acid, such as a DNA, preferably a genomic DNA, or an RNA, with the method comprising:

(a) digesting the nucleic acid (i.e., the original molecule), such a genomic DNA, at the 3' end of a region of interest to obtain a digested nucleic acid;

(b) performing a linear amplification of the digested nucleic acid, such as a genomic DNA, with a primary barcoded adapter comprising a primary barcode to directly barcode the original molecule, where a regular DNA polymerase may be used in performing the linear amplification for sequencing DNA, where a reverse transcriptase may be used in (b) for sequencing a RNA;

(c) removing unused primary barcodes by digestion with a single-stranded DNA exonuclease to obtain a first product;

(d) performing N cycles of linear amplification of the first product using a plurality of secondary barcoded adapters, each of the plurality of secondary barcoded adapters comprising a secondary barcode;

(e) removing unused secondary barcodes to produce a second product comprising a first library of multiple copies of the original molecule, wherein the N cycles of linear amplification add the secondary barcode such that each primary barcode has N secondary barcodes;

(f) performing a mutant enrichment on the second product to obtain a second library; and (g) sequencing the second library.

In the above exemplary procedure (a), when the nucleic acid is a DNA, digesting the DNA may be performed by using an enzyme. Examples of the enzyme that can be used to digest the DNA include a restriction enzyme and other types of nucleases such as CRISPR/Cas9.

In the above procedure (a), when the nucleic acid is an RNA, digesting the RNA may be performed by using an enzyme. Examples of the enzyme that can be used to digest the RNA include RNAse H and eukaryotic Argonaute.

The removing unused secondary barcodes may be performed by either by additional one cycle of PCR with a reverse amplifier to protect single-stranded linear amplification products followed by digestion with a single-stranded DNA exonuclease, or by size selection, for example, using beads, gel and/or column purification.

The exemplary method may further utilize an exponential polymerase chain reaction (PCR) of the linear amplification product between the removal of the unused secondary barcodes and the performance of the mutant enrichment.

According to certain exemplary embodiments of the present disclosure, the exemplary method may further include performing an analysis of a data obtained in the above sequencing procedure (g). The data analysis may include, for example, grouping reads by the primary barcode (R) into a plurality of groups and plurality of groups and considering the number of primary barcodes R, building consensus, considering the number of the secondary barcodes (S) and R for each group, and calling for mutants.

In another exemplary embodiment, a method can be provided for sequencing an RNA, the method comprising:
(a) digesting the RNA at the 3' end of a region of interest to obtain a digested nucleic acid;
(b) performing a linear amplification of the digested RNA with a primary barcoded adapter comprising a primary barcode to directly barcode the original molecule, wherein a reverse transcriptase may be used in (b);
(c) removing unused primary barcodes by digestion with a single-stranded DNA exonuclease to obtain a product;
(d) performing exponential PCR of the product obtained in (c) to obtain a product; and
(e) sequencing the product obtained in (d).

In the above exemplary procedure (a), digesting the RNA can be performed by using an enzyme. Examples of the enzyme that may be used to digest the RNA include RNAse H and eukaryotic Argonaute.

In further exemplary embodiments of the present disclosure, the method may include the following features: (a) a unique implementation of secondary barcodes prior to mutant enrichment to protect against polymerase errors; (b) a mutant enrichment process; and/or (c) a unique generalizable method for data analysis of double barcoded sequences.

The exemplary mutant enrichment in procedure f) may include:
1) generating single stranded DNA from the second product
2) annealing a reverse-complement wild type sequence that does not overlap the degenerate regions of the first library to form homo- or heteroduplexes that correspond the wild-type or mutant sequences respectively;
3) digesting homoduplexes using a duplex specific nuclease to generate an enriched product
4) repetition of 2) and 3) to further increase enrichment;
5) exponential PCR amplification of the enriched product; and
6) analysis of the data obtained in step f), comprising grouping reads by the primary barcode (R) and considering the number of primary barcodes R, building consensus sequences, considering the number of the secondary barcodes (S) and R for each grouping, and calling for mutants.

Exemplary mutant enrichment of primary and secondary barcoded sequences can be performed as described or by any other method.

In another exemplary embodiment of the present disclosure, a method can be provided for sequencing a genomic DNA, comprising:
(a) digesting the genomic DNA at a 3' end of a region of interest to obtain a digested genomic DNA;
(b) performing a single cycle of linear amplification of the digested genomic DNA with a primary barcoded adapter comprising a primary barcode, where a regular DNA polymerase may be used in the performance of the single cycle for sequencing a DNA, and where a reverse transcriptase may be used in procedure (b) for sequencing a RNA;
(c) removing unused primary barcode by digestion with a single-stranded DNA exonuclease to obtain a first product;
(d) performing N cycles linear amplification of the first product using a plurality of secondary barcoded adapters, each of the plurality of secondary barcoded adapters comprising a secondary barcode, to obtain primary and secondary barcoded molecules;
(e) performing exponential PCR of the primary and secondary barcoded molecules to obtain a library comprising exponential PCR amplified primary and secondary barcoded molecules;
(f) generating single stranded DNA from the exponential PCR amplified primary and secondary barcoded molecules;
(g) annealing the single stranded primary and secondary barcoded molecules to a wild-type sequence that does not overlap a degenerate region of the library to form annealed molecules each having an annealed region;
(h) cleaving homoduplex molecules with duplex specific nuclease to obtain an enriched product;
(i) repetition of procedure (g) and (h) to further enrich the library;
(j) amplifying the enriched product to obtain an amplified product;
(k) sequencing the amplified product; and
(l) analyzing the data obtained in procedure (k).

According to further exemplary embodiments, systems, kits and computer-accessible medium can be provided to perform the exemplary procedures described herein using computer software and hardware processors.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1:
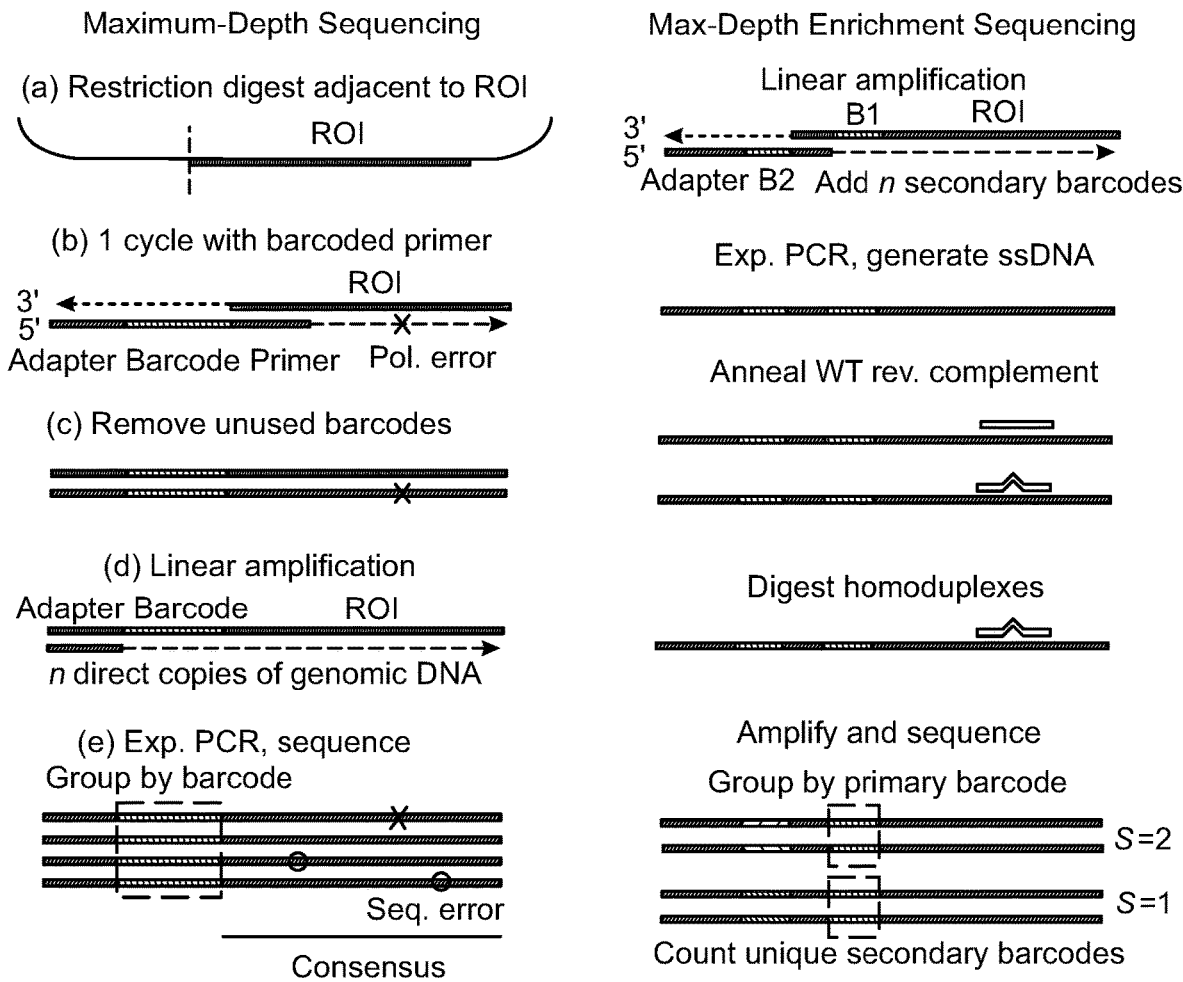
FIG. 1 is an illustration of an exemplary comparison of maximum depth enrichment sequencing (MDES) with maximum-depth sequencing (MDS) according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the certain exemplary embodiments illustrated in the figures and the appended claims.

DETAILED DESCRIPTION OF EXEMPLARY EMBODIMENTS

Maximum depth enrichment sequencing (MDES) as described herein according to certain exemplary embodiments can be broadly applicable as an extension to any sequencing method and/or procedure that utilizes barcoding such as, e.g., MDS, and any other derivatives. As an example, the adaptation of this exemplary procedure to MDS is described herein, because it is the current most sensitive and specific technology. A more detailed discussion of MDS can be found in, e.g., Jee et al., Rates and mechanisms of bacterial mutagenesis from maximum-depth sequencing, Nature 534, 693-6 (2016) and U.S. Patent Application Publication No. 2017/0016062, the disclosure of which are hereby incorporated by reference in their entireties.

FIG. 1 shows an illustration of a comparison of maximum depth enrichment sequencing (MDES) with maximum-depth sequencing (MDS) according to an exemplary embodiments of the present disclosure. For example, MDS involves (a) digestion of genomic DNA at the 3' end of a region of interest, (b) linear amplification of the digested genomic DNA with a barcoded adapter to directly barcode the original molecule, (c) removal of unused barcodes by digestion with an single-stranded DNA exonuclease, (d) N cycles linear amplification of this product to produce several copies of the original molecule, (e) exponential polymerase chain reaction (PCR) of the linear amplification product, and (f) sequencing of the final library. The barcode can be denoted from the unmodified MDS protocol as the primary barcode (B1).

In the exemplary adaptation of MDS to MDES, a secondary barcode (B2) should be added during (d) N cycles of linear amplification such that each primary barcode family has N subfamilies, each labeled by a unique secondary barcode. Following this, unused secondary barcodes should also be removed. Because linear amplification produces single stranded products, bead selection or column cleanup should be used instead of a single-strand DNA exonuclease. Alternatively or in addition, a single round of PCR can be performed with short primers targeting the end of the single strand linear products before a second round of single-strand DNA digestion. The exemplary purpose of these secondary barcodes is discussed in more detail herein.

Following (e) exponential PCR of these primary and secondary barcoded molecules, single stranded DNA can be generated by any suitable method. One exemplary method includes biotinylation and immobilization of one strand of the library, and then removal of the complementary strand with alkaline conditions. Single stranded primary and secondary barcoded molecules can then be annealed to a wild-type reverse complement sequence that does not overlap the degenerate regions of the library to form homo and heteroduplexes that correspond to wild-type and mutant sequences respectively. Subsequently, a duplex specific nuclease can be used to digest wild-type homoduplexes, effectively enriching mutant sequences by negative selection which are then amplified for sequencing.

In this exemplary case, duplex specific nuclease isolated from the Kamchatka crab is used for enrichment. The exemplary mutant enrichment step is performed in a similar manner to the method: NaME-PrO—ablation of WT sequences (Song, C. Elimination of unaltered DNA in mixed clinical samples via nuclease-assisted minor-allele enrichment. Nucleic Acids Res. 44(19): e146 (2016)). However, the exemplary approach applies the enrichment step to single-stranded primary and secondary barcoded molecules while NaME-PrO applies enrichment directly to unmanipulated genomic DNA. Alternatively or in addition, the exemplary mutant enrichment of primary and secondary barcoded molecules can be performed using positive selection with a mismatch nuclease such as CELII or with any other methods.

Following sequencing, the exemplary analysis workflow is like MDS in that it can include grouping primary barcodes into families and calling for a consensus sequence. Typically, the number of reads for each primary barcode is recorded as "R", filtering is done to find families, for example, with $R \geq 3$, a consensus sequence is found, and mutations are identified. It is possible to refer to MDS documentation for details in the selection of $R \geq 3$ and the calculated error rate. MDS documentation includes, and is not limited to, U.S. Patent Publication No. 2017/0016062; European Patent Publication No. 2107124; The TRACERx consortium et al. Phylogenetic ctDNA analysis depicts early-stage lung cancer evolution. *Nature* 545, 446-451 (2017); and Jee, J. et al. Rates and mechanisms of bacterial mutagenesis from maximum-depth sequencing. Nature 534, 693-6 (2016), the disclosures of which are incorporated herein by reference in their entirety.

For MDES, notable additions to the analysis workflow can include, e.g., retaining the number of unique secondary barcodes (denoted as "S") in each primary barcode family, modified calling for consensus sequences, filtering for true mutants, and estimating the mutant frequency.

Figure 2:
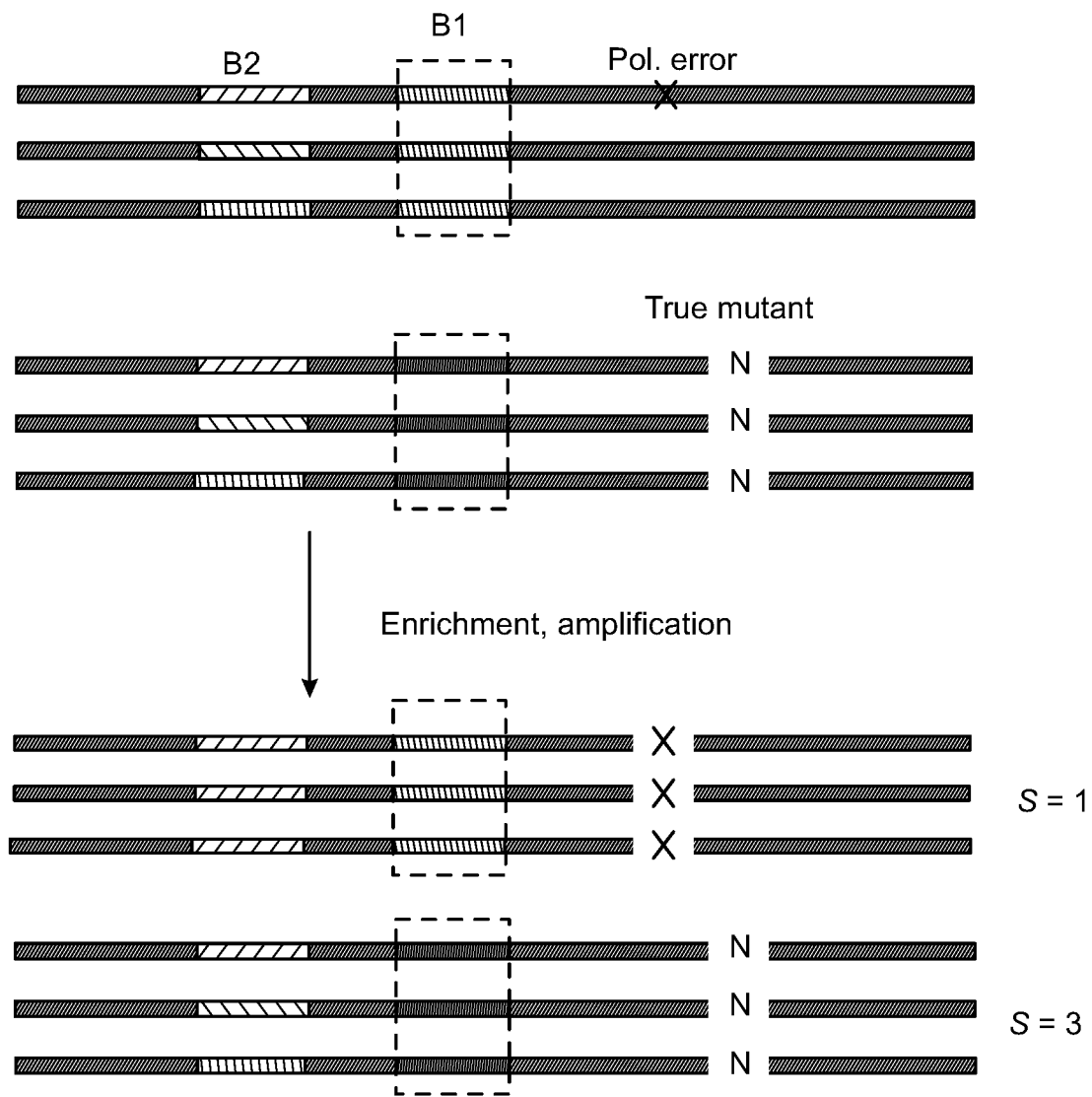
FIG. 2 is an illustration of secondary barcoding preserving the ability to identify polymerase errors following mutant enrichment, according to an exemplary embodiment of the present disclosure.

FIG. 2 shows an illustration that secondary barcoding preserves the ability to identify polymerase errors following mutant enrichment, according to an exemplary embodiment of the present disclosure. The exemplary use of secondary barcoding can be important for correctly identifying mutants in the method according to certain exemplary embodiments of the present disclosure. This can be because any method that aims to enrich for mutants after barcoding and amplification loses the ability to call for a consensus sequence. For example, it is possible to utilize a true wild-type primary barcode family where a polymerase error is made in a single copy during (d) N cycles of linear amplification. Assuming proportional exponential amplification, 1/N of the family would contain this error. With MDS, a majority vote strategy when calling consensus would properly call this as a wild-type sequence. However, if mutant sequences are enriched and selected for, the wild-type sequences are lost and MDES would erroneously call this a mutant sequence. By counting the number of unique secondary barcodes in a primary barcode family, the false positive error rate can be calculated to be EAS, with E being the estimated probability of a polymerase error occurring per nucleotide. As E is less then 1E-6 for modern DNA polymerases, this value clearly decreases to insignificant levels with, for example, $S \geq 2$. In certain exemplary embodiments, the threshold for S can be increased to further decrease the false positive error rate.

Figure 3:
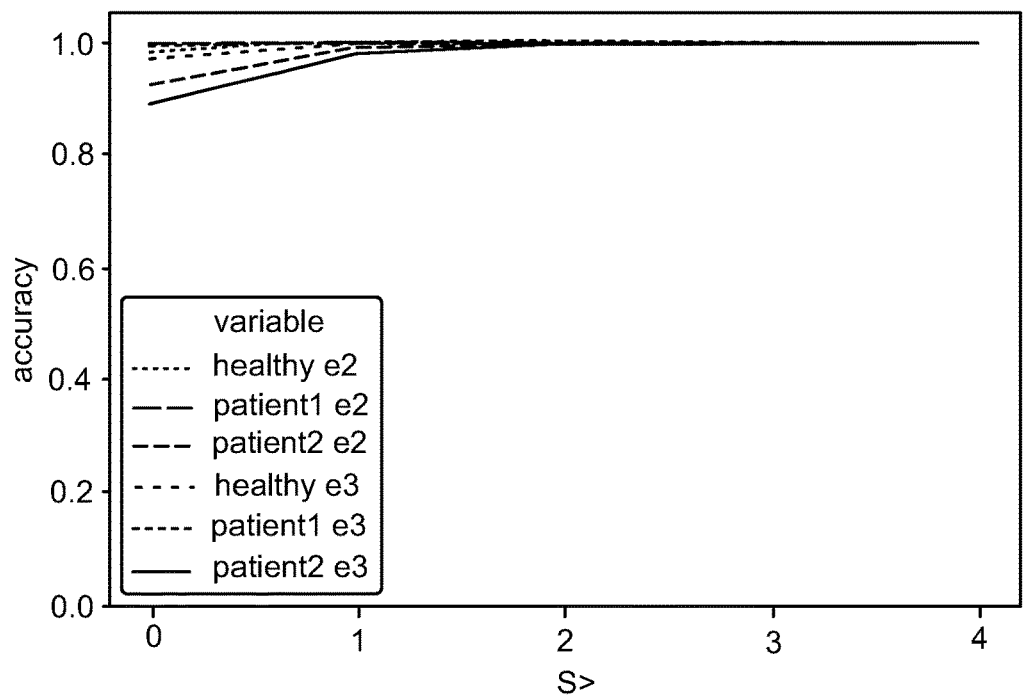
FIG. 3 is an illustration of a high accuracy of an exemplary embodiment of the present disclosure in genomic DNA collected from three patient buffy coat samples when compared to MDS. Accuracy is increased as the secondary barcode threshold "S" is increased. "e2" and "e3" signify two and three repetitions of the mutation enrichment step, respectively.

FIG. 3 is an illustration of a high accuracy of an exemplary embodiment of the present disclosure when compared to MDS. MDS and MDES libraries were prepared from genomic DNA isolated from three patient buffy coat samples in a way such that consensus sequences sharing the same primary barcode would be identical between each method. Because MDS is well established as a highly accurate method, it is used as ground truth when benchmarking the enriched method. As expected, accuracy of the enriched method is increased as the secondary barcode threshold "S"

is increased to ≥2. The labels "e2" and "e3" signify repetition of the mutant enrichment step two and three times respectively.

Figure 4:
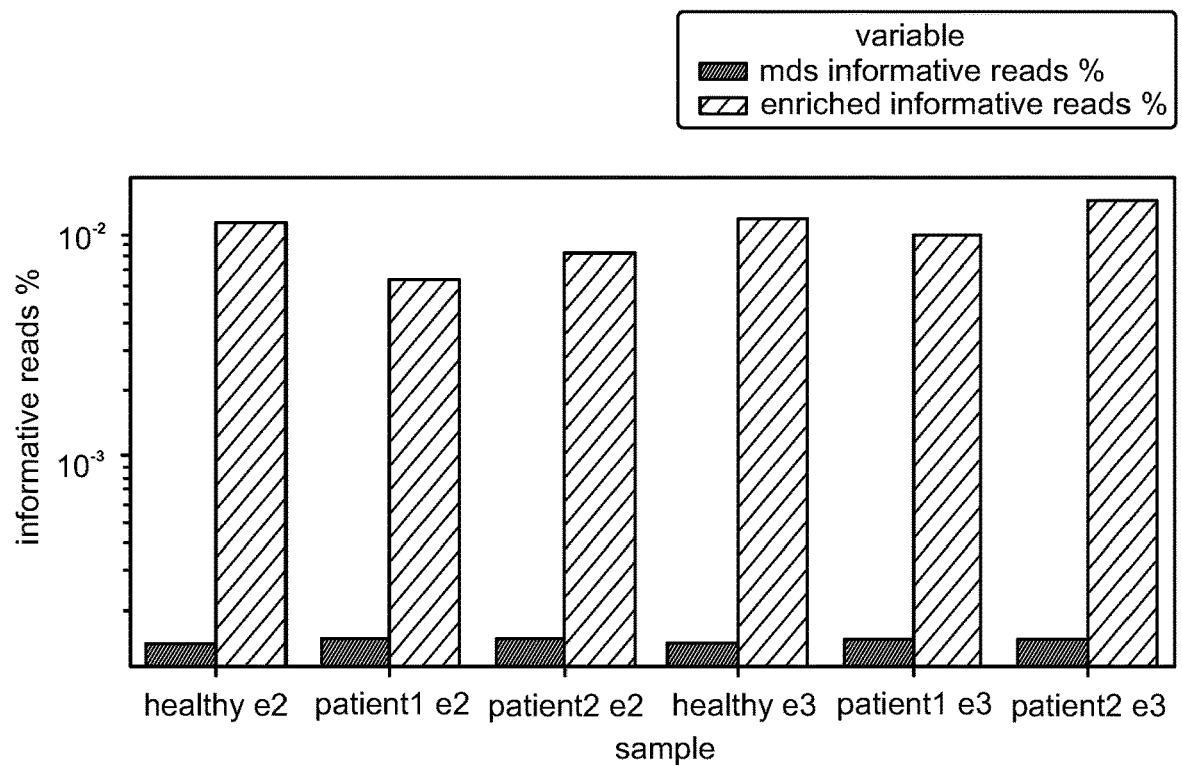
FIG. 4 is an illustration demonstrating a two orders of magnitude enrichment of mutation informing reads following an exemplary embodiment of the present disclosure in genomic DNA collected from three patient buffy coat samples. "e2" and "e3" signify two and three repetitions of the mutation enrichment step, respectively.

FIG. 4 is an illustration demonstrating a two orders of magnitude enrichment of mutation informing reads in an exemplary embodiment of the present disclosure when compared to MDS with R≥3 and S≥2. This corresponds to a near 100 fold decrease in sequencing space and costs when using MDES with the same accuracy and sensitivity MDS affords, or a 100 fold increase in sensitivity if the amount of sequencing space is kept constant.

Thus, the exemplary strategy for analysis of MDES data is then to group families by primary barcode, vote for consensus sequences, and record R and S. After selecting for sequences with satisfactory R≥3 and S≥2, mutants can be confidently identified to the same accuracy of MDS with greater than 100 fold increase in read efficiency.

In summary, the methods and procedures according to an exemplary embodiment according to the present disclosure can address the various deficiencies in the prior methods and systems, and can comprise, e.g.: secondary barcoding of primary barcoded molecules in order to preserve error correction throughout mutant enrichment, removal of unused secondary barcodes, annealing of barcoded libraries to known wild-type sequences to form homo or heteroduplexes, duplex specific nuclease digestion of the aforementioned primary and secondary barcoded duplexes, amplification of the remaining mutant products, and sequence analysis using a strategy in which the number of unique secondary barcodes per primary barcode are counted and taken into consideration. These exemplary features according to various exemplary embodiments of the present disclosure may be applied to other barcoding methods with minimal adjustment.

To reiterate the exemplary improvements upon existing technologies described herein, MDES increases the sensitivity and efficiency of rare mutant detection far beyond any current methods. Certain competing technologies include other barcoding methods such as duplex sequencing and MDS, but these conventional technologies are prohibitively expensive for widespread adoption and are likely only reasonably sensitive to 5E-5. Certain disadvantages of other NGS error-correction methods are discussed in, e.g., Jee et al., Rates and mechanisms of bacterial mutagenesis from maximum-depth sequencing. Nature 534, 693-6 (2016).

MDES according to various exemplary embodiments of the present disclosure can be used to make any amplicon barcoding method more sensitive and more affordable. One of certain important applications is in cancer prognosis and screening. As described herein, MDES according to various exemplary embodiments of the present disclosure can decrease costs more than 100-fold, allowing for affordable screening of thousands of ROI. This exemplary technology can provide early detection of initiating mutations, relapse, and resistance in cancer from a single blood draw. Additional exemplary applications are described in U.S. Patent Application Publication No. 2017/0016062, e.g., paragraph [0033], the entire disclosure of which is incorporated herein by reference.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference, in their entireties:
1. U.S. Patent Publication No. 2017/0016062
2. European Patent Publication No. 2107124
3. The TRACERx consortium et al. Phylogenetic ctDNA analysis depicts early-stage lung cancer evolution. *Nature* 545, 446-451 (2017)
4. Jee, J. et al. Rates and mechanisms of bacterial mutagenesis from maximum-depth sequencing. Nature 534, 693-6 (2016)
5. Song, C. Elimination of unaltered DNA in mixed clinical samples via nuclease-assisted minor-allele enrichment. Nucleic Acids Res. 44(19): e146 (2016).)

What is claimed is:
1. A method for sequencing a nucleic acid, comprising:
(a) digesting the nucleic acid that includes an original molecule at a 3' end of a region of interest to obtain a digested nucleic acid;
(b) performing a linear amplification of the digested nucleic acid with a primary barcoded adapter comprising a primary barcode to directly barcode the original molecule;
(c) removing unused primary barcodes by a digestion with a single-stranded DNA exonuclease to obtain a first product;
(d) performing a plurality of cycles of a linear amplification of the first product using a plurality of secondary barcoded adapters, each of the plurality of secondary barcoded adapters comprising a secondary barcode;
(e) removing unused secondary barcodes to produce a second product comprising a first library of multiple copies of the original molecule, wherein the cycles of the linear amplification add the secondary barcode such that each of the primary barcodes has a plurality of secondary barcodes, wherein a number of the cycles of the linear amplification is the same as a number of the secondary barcodes in each of the primary barcodes;
(f) after procedure (e), performing a mutant enrichment on the second product to obtain a second library; and
(g) sequencing the second library.
2. The method of claim 1, further comprising:
performing a data analysis of the sequenced second library, wherein the performance of the data analysis includes grouping reads by the primary barcode (R) into a plurality of groups, filtering for sufficient R, building consensus sequences, considering the number of the secondary barcodes (S) and R for each group, and calling for mutants.

3. The method of claim 1, wherein the removal of the unused secondary barcodes is performed by (i) an additional one cycle of PCR with a reverse amplifier to protect single-stranded linear amplification products followed by digestion with a single-stranded DNA exonuclease, or (ii) a size selection using beads, gel or column purification.

4. The method of claim 1, wherein procedure (a) when the nucleic acid is DNA comprises digesting the DNA at the 3' end of the region of interest with an enzyme.

5. The method of claim 4, wherein the enzyme is a restriction enzyme or CRISPR/cas9.

6. The method of claim 1, wherein procedure (a), when the nucleic acid is RNA, comprises digesting the RNA at the 3' end of the region of interest with an enzyme.

7. The method of claim 6, wherein the enzyme is at least one of RNAse H or eukaryotic Argonaute.

* * * * *